United States Patent [19]

Jatteau et al.

[11] 4,342,916

[45] Aug. 3, 1982

[54] METHOD OF AND APPARATUS FOR TOMOGRAPHIC EXAMINATION OF STRUCTURES BY X-RAY OR GAMMA RAY SCANNING

[75] Inventors: Michel Jatteau, Lésigny; Vincent Chalmeton, Yerres; Joseph Pauvert, Ris-Orangis, all of France

[73] Assignee: U.S. Philips Corporation, New York, N.Y.

[21] Appl. No.: 99,761

[22] Filed: Dec. 3, 1979

[30] Foreign Application Priority Data

Nov. 27, 1978 [FR] France ................................ 78 33430

[51] Int. Cl.³ .......................................... G01N 21/00
[52] U.S. Cl. ..................................................... 378/4
[58] Field of Search ............ 250/312, 320, 321, 363 S, 250/445 T

[56] References Cited

U.S. PATENT DOCUMENTS 3,106,640 10/1963 Oldendorf ........................... 250/320
4,124,804 11/1978 Mirell ............................... 250/363 S
4,150,292 4/1979 Ter-Pogossian ................. 250/363 S

*Primary Examiner*—Davis L. Willis
*Attorney, Agent, or Firm*—Thomas A. Briody; Robert T. Mayer; Jack E. Haken

[57] ABSTRACT

A method of and an apparatus for tomographic examination by X-ray or gamma ray scanning of structures, intended for the display of images of slices of the structure examined by determination of the electron density in each volume element of these slices.

Using an X-ray or gamma ray source, a stationary principal detector and an auxiliary detector which is aligned with the source, for each volume element of each slice two measurements are performed of the diffusion by the Comption effect towards the principal detector and two measurements are performed of the transmission between the source and the auxiliary detector, starting with the slice nearest to the principal detector and proceeding to the slice which is situated furthest from this detector. The measuring results are progressively used for calculating the exact electron density throughout the structure examined.

11 Claims, 12 Drawing Figures

METHOD OF AND APPARATUS FOR TOMOGRAPHIC EXAMINATION OF STRUCTURES BY X-RAY OR GAMMA RAY SCANNING

The present invention relates to a method of tomographic examination by X-ray or gamma ray scanning of structures such as biological tissues, for diagnostic purposes, or of materials for non-destructive examination of their internal structure; the invention also relates to an apparatus for performing this method. The method and the apparatus in accordance with the invention notably serve to enable the display of images of slices of a part of the human body by determination of the electron density in each volume element of these slices, that is to say by means of a densitometric method.

Conventional radiology produces a flat image of a three-dimensional object, said image resulting from the superposition, by projection on a carrier, of the shadow images of the various internal structures of this object which are traversed by an incident X-ray beam. When examination of organs is concerned, the beam which emerges from the body of the patient contains an accumulation of data concerning the absorption of the incident beam which data depend more or less of the differences in shape, thickness and nature of all the organs encountered and also of the wavelength of the radiation. On the film or screen on which the emerging data carrying beam is to be incident, the differences in shape generally appear with satisfactory sharpness and adequate contrast, but this is not the case for the differences in thickness or nature. In order to mitigate these insufficiencies, radiologists practice given interventions, such as opacification or injection of substances, but most of these are uncomfortable for the patient.

In order to avoid these interventions and to reduce at the same time the loss of data which is inherent of a conventional tomographic examination of organs (examination where in principle the quasi-totality of the data recovered at a large number of different angles is eliminated in order to save only the data which relate to a single layer which is to be especially observed), use is increasingly made of a technique which combines radiology and data processing: tomodensitometry, or computerized tomography. A computerized tomographic apparatus enables examination of organs, without interventions which are uncomfortable to the patient, by determination of the density of the living matter in generally transversal slices of the patient. Computerized tomography essentially consists in that a very large number of attenuation measurements are performed, mostly during synchronized displacements of the radiation source and the associated detection device which are successively performed as often as necessary. The series of measurements is subsequently treated by a computer in order to reconstruct the image of the examined zone.

X-ray computerized tomographic apparatus realized thus far, however, have a mediocre precision, because the emission of the photons is neither mono-energic nor very stable, this giving rise to approximations of the attenuations measured. Moreover, the unprecision of the mechanical movements during the scanning gives rise to systematic errors, or artefacts, and to a deterioration of the resolution and the legibility of the ultimate image. Finally, the image in the form of a pattern of electron densities does not become available until after a very large number of measurements has been performed, the treatment of which requires extensive and expensive data processing means.

The invention has for its object to propose a method of and an apparatus for tomographic examination by means of X-rays or gamma rays which, without either involving disagreeable interventions of excessive and hence harmful irradiation for the patients, permits fast execution of the desired examination and notably offers a reduction of the time required for the calculation of the electron densities, said calculations being very accurately performed.

To this end, the invention relates to a method of tomographic examination of the kind defined above and is characterized in that the method comprises the following steps:

a = scanning a first slice with a collimated beam of penetrating radiation of known intensity in a first direction, whereby said beam extends within said slice.
= thereby detecting radiation within said beam, which radiation has passed through the slice, for obtaining a first set of measuring data $n_1$,
= and simultaneously detecting Compton-scattered radiation emerging from each element in said slice, which detected radiation leaves the body in a direction perpendicular to said slice, for obtaining a second set of measuring data $n_2$, b = scanning the first slice with a substantial identical beam of penetrating radiation in a direction opposite the first direction, whereby the beam extends within said slice,
= thereby at least detecting Compton scattered radiation from each element in said slice, which radiation leaves the body in the direction perpendicular to said slice, for obtaining a third set of measuring data $n_3$, c = storing the first, second and third sets of measuring data d = determining an electron density value for each element in said slice on the basis of at least the first, second and third set of measuring data, e = storing the electron density value for each element in said slice f = scanning a further slice adjacent to the slice scanned previously and detecting radiation as defined in a and b for obtaining at least a further first, second and third set of measuring data for said further slice, g = storing said further sets of measuring data h = determining an electron density value for each element in said further slice on the basis at least the further first, second and third sets of measuring data thereby utilizing the electron density values determined previously, i = storing the electron density values for each element in said further slice, j = repeating the steps sub f, g, h, i and j for each slice adjacent to the slice scanned previously for all slices within the part of the body to be examined, k = displaying the electron density values of each element of any of the slices.

The use of such a densitometric tomography method by photon scattering is advantageous from a number of points of view. Actually, contrary to the case described above which involves computer tomography by transmission of an X-ray or gamma ray beam where only a very large number of attenuation measurements enables the computer, after complex and long calculations, to reconstruct a pattern of the spatial variations of the electron density of the tissues examined, the signal used is in this case formed by a number of detected photons (this detection takes place after scattering inside the volume element) which is directly proportional to the variations of the electron density which are to be observed. Moreover, the risk of detection of photons which have been subjected to multiple scattering in the same detection direction in the examined tissues is small, thus ensuring substantial insusceptibility of the measurements to these disturbing phenomena.

As the patient is scanned in two directions for each slice to be examined the quality of radiation exposed to the patient is severely reduced relative to the radiation quantity to any computer tomographic apparatus, in which each slice to be examined has to be irradiated some hundred times.

On the other hand, the simplicity of the calculations and their realization in real time, that is to say for a given slice of the examined zone, during the acquisition time of the results which are to be used for the calculations concerning the next slice, reduces the useful capacity of the memory. The computer means utilized, therefore, may be much simpler and hence less costly.

The invention also relates to a tomography apparatus for performing the method described above. This tomography apparatus for examination of structures by X-ray or gamma ray scanning is characterized in that the apparatus comprises:

at least one collimated radiation source for generating a beam of penetrating radiation in a first direction for scanning a slice of a body, whereby said beam extends within the slice, at least one collimated principal radiation detector for detecting radiation emerging from the slice and leaving the body in a direction perpendicular to the first direction, at least one collimated auxiliary radiation detector for detecting radiation leaving the slice within said beam, a scanning control unit for controlling the scanning of the slice with at least the one source and the detectors, a data acquisition unit for gathering at least first, second and third sets of measuring data, a memory for storing at least said sets of measuring data, a data processing device for determining from at least said first, second and third sets of measuring data electron density values in elements in the scanned slice and a display device for displaying the electron density values, which have been determined.

Other aspects and advantages of the method and the apparatus in accordance with the invention will be better understood on the basis of the following description and the accompanying drawings which show, by way of non-limitative examples, various embodiments in accordance with the invention.

The tomography method described with reference to the FIGS. 1 to 7 serves to enable the display of images of slices of a zone 1 of the human body. For performing this method, use is essentially made of an X-ray or gamma ray source 2, a stationary principal detector 3 and an auxiliary detector 4, as well as of a scanning control device, a data processing device, a device for displaying the electron density values and a general control device which will be described in detail hereinafter.

The source 2, comprising a collimator, serves to emit radiation having a narrow spectrum and a given but arbitrary central frequency towards the zone 1 to be examined. The radiation is emitted in the form of a cylindrical beam 10 which has a central axis 11 and which contains a known number of $n_o$ protons, the source 2 having an energy which is sufficient to ensure that the Compton diffusion (deviation of a photon of given energy when it encounters an electron in the traversed zone) is the predominant effect of the interaction between these emitted photons and the electrons encountered thereby inside the zone 1.

The stationary principal detector 3, comprising collimators 12 whose longitudinal axes extend perpendicularly to the central axis 11 of the beam 10 emitted by the source 2, serves to supply these different types of data: on the one hand two data which permit localization of the position of each detected photon, and on the other hand a third data in the form of an amplitude signal whch is proportional to the energy of the detected photon.

The auxiliary detector 4 is arranged so that its longitudinal axis coincides with the central axis 11 of the beam 10 and that the source 2 and this detector thus aligned are, moreover, situated one on each side of the zone 1 to be examined.

The method in accordance with the invention comprises the following operations:

(A) Using the source 2 and the detectors 3 and 4, three distinct measurements are performed for each volume element $E_i$ encountered by the beam 10 in the zone to be examined in the irradiated slice $S_1$ which is nearest to the principal detector. This slice $S_1$ is shown notably in the FIG. 3 and extends perpendicularly to the axes of the collimators 12 of the principal detector 3. The irradiation is effected at will be linear scanning (FIG. 1) or circular scanning (FIG. 2) around the zone to be examined. The localization of the position permitted by this detector 3 is defined with respect to a reference localization X, Y, Z visible in the FIGS. 1 and 2, the plane X, Y thereof being parallel to the central plane P of the slice $S_1$ (the axis Z extends parallel to the axes of the collimators 12) and of all the slices $S_j$ which are to be successively irradiated by the source 2. The volume elements Ei constituting each slice are parallelepipeds of small dimensions which are defined by the fixed elementary detection angle of the collimators of the principal detector and by the thickness of the slice. This thickness generally has a value which approximates that of the diameter of the collimators, but may be changed in accordance with the nature of the examination. For example, a first examination can be performed with a given thickness of the slices in order to find the absorption coefficients of the tissues throughout the zone to be examined, after which a second, more detailed examination is performed of only a part of the zone which is realized by adopting a smaller thickness of the slices in order to obtain a more refined analysis. The three distinct measurements associated with each volume element of the zone to be examined are the following: measurement of a data $n_1$ of photons transmitted by the source 2 to the auxiliary detector 4 while traversing all the volume elements encountered (see FIG. 4 in which the transmitted beam of photons which reaches the detector 4 is denoted by the reference numeral 10a) of which the volume element $E_i$ is notably considered, measurement of a data $n_2$ of photons scattered by the Compton effect from the volume element $E_i$ to the principal detector 3 (see FIG. 5 in which the beam of photons scattered substantially 90° which reaches the detector 3 is denoted by the reference numeral 10b) and, after permutation of the relevant positions of the source 2 and the auxiliary detector 4 with respect to the zone 1, measurement of a data $n_3$ of photons scattered by the Compton effect from the same volume element $E_i$ to the principal detector 3 (see FIG. 6 in which the beam of photons scattered substantially 90° which reaches the detector 3 is denoted by the reference numeral 10c). It is to be noted that, as from now, contrary to the measurement of $n_2$ and $n_3$, the measurement of $n_1$ is identical, except for statistical fluctuations, for each of the volume elements $E_1$ encountered by the beam 10 for a given position of the source 2 and the associated auxiliary detector 4. For the sake of simplicity, therefore, for said given position only one measurement of $n_1$ is performed which is valid for each of the elements $E_i$ encountered. This remark is applicable throughout the description, be it that it is still possible, of course, to perform a distinct measurement of $n_1$ for each volume element encountered, (B) Using a data processing device, the detailed description of which will be given at a later stage, the results of the three measurements are derived as soon as they are supplied by the principle detector 3 and the auxiliary detector 4, after which the exact value of the electron density in each volume element $E_i$ of the slice $S_1$ examined is calculated and stored in the memory. For each element $E_i$ of an arbitrary slice, the density $d_{i,j}$ (x, y, z) is given by the relation (1) as follows:

$$d_{i,j} = \frac{n_2 + n_3}{k \cdot n_0 \cdot dx \cdot T_{i,j} \cdot \left(\sqrt{\frac{n_2}{n_3}} + \sqrt{\frac{n_3}{n_2}}\right) \cdot \sqrt{\frac{2n_1}{n_0}}} \quad (1a)$$

This formula (1a) can easily be rewritten (by multiplying the numerator and the denominator with a quantity $\sqrt{n_2 \cdot n_3}$:

$$d_{i,j} = \frac{1}{k \cdot dx \cdot T_{ij}} \cdot \sqrt{\frac{n_2 \cdot n_3}{2 n_0 \cdot n_1}} \quad (1)$$

In this relation, $n_0$, $n_1$, $n_2$, $n_3$ have already been defined, and dx represents the dimension of the volume element in the direction of propagation of the incident beam 10 emitted by the source 2. The term $T_{i,j}$(x, y, z) takes into account the transmission of the radiation diffused through 90° by the relevant volume element towards the superposed tissues between this volume element and the principal detector 3, and can be expressed by a relation (2) as follows:

$$T_{i,j} = T_{i,j-1} \cdot e^{-S \cdot d_{i,j-1} \cdot dz} \quad (2)$$

in which S represents the effective overall diffusion section, dz the thickness of each slice $S_j$ of the zone to be examined, and $d_{i,j-1}$ (x, y, z) the value of the electron density already calculated for the volume element of the slice previously irradiated which contacts the volume element considered. In accordance with the invention, the analysis of the zone 1 to be examined is started by first irradiating the slice $S_1$ which is situated nearest to the principal detector 3: for this slice, all photons diffused by 90° by the volume element considered reach the detector 3, which means that $T_{i,1}$ (x, y, z)=1. The exact calculation of the values of the electron density in each volume element of the slice $S_1$ can thus be realized on the basis of equation (1).

Figure 1:
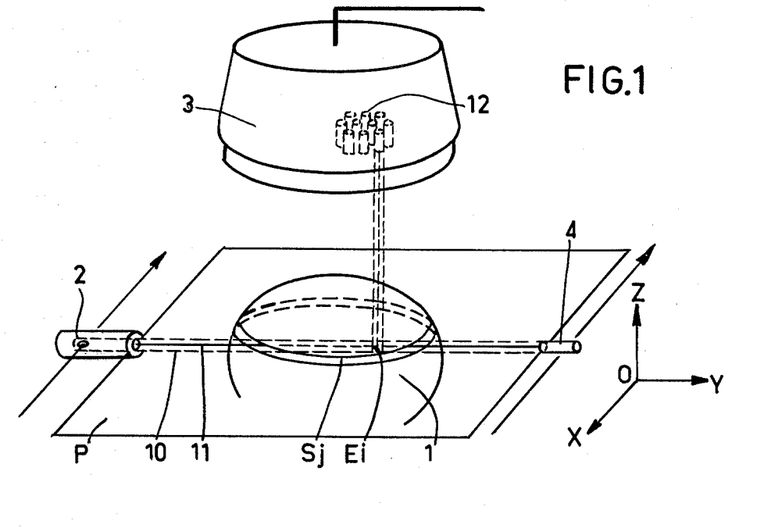
FIGS. 1 and 2 show diagrams to illustrate the principle of the tomography method in accordance with the invention in the case of a rectilinear scan (FIG. 1) and a circular scan around each slice of the zone to be examined (FIG. 2)
Figure 2:
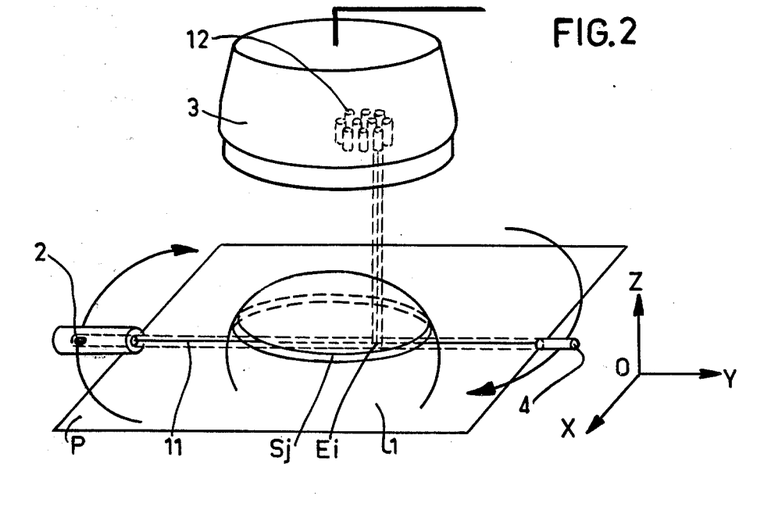
Figure 3:
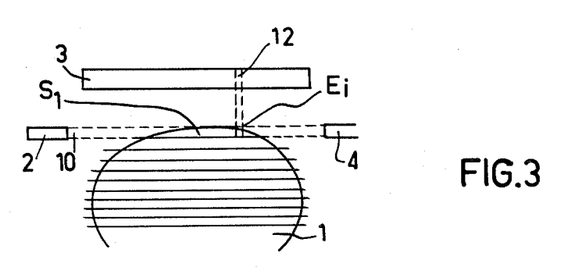
FIG. 3 shows the first examination phase, that is to say the irradiation of the slice of the zone to be examined which is nearest to the principal detector.
Figure 4:
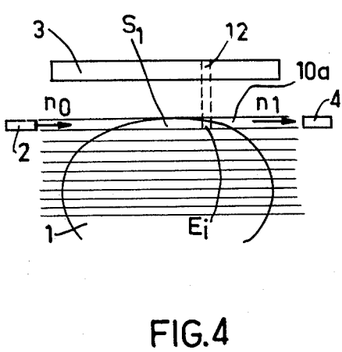
FIGS. 4 to 7 show the four types of measurements which can be performed by means of the method and the apparatus in accordance with the invention.
Figure 5:
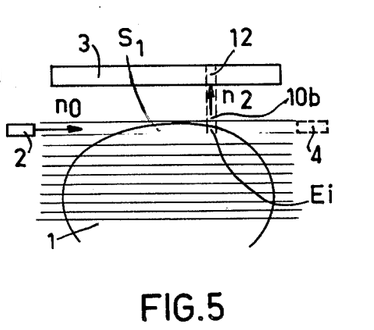
Figure 6:
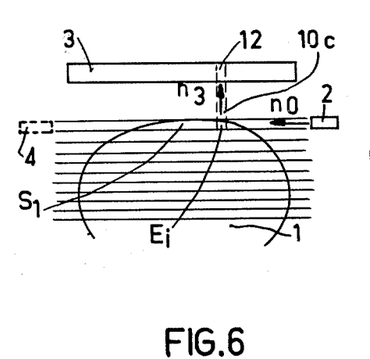

(C) In each new slice $S_j$ which is successively encountered in the zone 1 to be examined and which is situated progressively further from the principal detector 3, the three distinct measurements of $n_1$, $n_2$ and $n_3$ performed sub (A) and diagrammatically shown in the FIGS. 4, 5 and 6 are repeated. On the basis of the new measuring results obtained and used by the data processing device as soon as they are supplied by the principal detector 3 and the auxiliary detector 4, and also on the basis of the electron density value in each volume element of the previously irradiated slice $S_{j-1}$, the exact value of the electron density in each volume element of this new slice $S_j$ is calculated and stored in the memory. This density is given by equation (1), in which the term $T_{i,j}$ (x, y, z) is given by equation (2). The process is identical for each slice, and it will be clear that the densities can be calculated for each volume element of a slice like they have already been calculated for each volume element of the preceding slice (that is to say situated between this slice and the principle detector (3).

(D) Using an image display device, it is possible to display the stored electron density values which correspond to an arbitrary slice $S_j$ of the zone 1 examined. The display of an image or a pattern is thus obtained in which the distribution of the electron densities in an arbitrary slice of the zone of the examined human body is shown.

Figure 7:
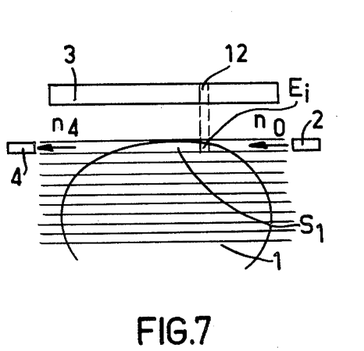

During the execution of the method, a fourth measurement may be performed in association with the three measurements of $n_1$, $n_2$, $n_3$ already described. This supplementary measurement is the measurement of the number $n_4$ of photons which, after execution of the permutation of the positions of the source 2 and the auxiliary detector 4 with respect to the zone 1, are transmitted from this source to this detector while passing through all the volume elements encountered (so the same volume element $E_i$ already considered for the three former measurements). The value $n_4$ thus obtained should in theory be identical to that of $n_1$. The differences observed in practice are due to small differences in collimation which may occur from one measurement to another, to the influence if photons which have been diffused a number of times, and particularly to statistical fluctuations inherent of the measurement itself. This fourth measurement, which is also subject to the remark given at the end of the foregoing section (A) concerning the number of measurements required, thus serves to make available a mean value $(n_1+n_4)/2$ which replaces $n_1$ in equation (1).

A tomography apparatus 20 for performing the methods described in detail in the foregoing will now be described with reference to FIG. 8. This apparatus 20 comprises a source 22a of gamma rays (for example, a cobalt 57 source), a principal radiation detector 23 which is a gamma camera, and an auxiliary radiation detector 24a which is an individual scintillator which is coupled to an individual photomultiplier tube. The source 22a comprises a collimator, and the principal detector 23 comprises collimators which extend parallel with respect to each other and perpendicularly to the axis 44a of the beam 42a emitted by this source. It is assumed hereinafter that the surface area of this principal detector 23 is so large that the entire zone to be examined, in the present case the head of a patient, is covered by the fixed elementary detection angles of the collimators of the principal detector 23.

The source 22a and the auxiliary detector 24a are aligned and are supported by supports 27 and 28, which are supported themselves by guide rods 29, 30 and 31, 32, respectively. The supports 27 and 28 can be simultaneously displaced for the irradiation of a given slice of the zone to be examined in a first scanning direction which extends perpendicularly to the axes of detection of the principal detector 23 (the longitudinal axes of the collimators); this displacement is realized by means of motors 33 and 34 which cause rotation of threaded spindles 35 and 36, respectively. The spindles 35 and 36 pass through the supports 27 and 28, respectively, and drive the supports in synchronism in order to maintain the alignment of the source 22a and the auxiliary detector 24a.

Transverse arms 37 and 38 constitute the frame of the apparatus which in its turn can be displaced in a second scanning direction which extends parallel to the detection axes of the principal detector 23 under the control of motors 39 and 40 (the motor 40 is not visible in FIG. 8) which drive threaded spindles 41 and 43, respectively. These spindles 41 and 43 provide the lifting or lowering of the transverse arms 37 and 38, respectively, said movements again being synchronized in order to ensure that the slices successively irradiated during the scanning remain in parallel.

For each volume element Ei considered in a slice of the zone to be examined, for example, the slice $S_j$ shown in FIG. 8, the measurements of the data $n_1$, $n_2$, $n_3$ defined in the description of the method in accordance with the invention, are executed as follows. The auxiliary detector 24a which is aligned with the source 22a supplies the data $n_1$ of photons of the cylindrical beam 42a emitted by the source 22a which have reached this detector. The stationary principal detector 23 enables the data $n_2$ of photons diffused towards this detector by the Compton effect to be obtained. Moreover, a second emission/detection assembly which is formed by a second source 22b (emitting a photon beam 42b having a central axis 44b) and a second auxiliary detector 24b (again an individual scintillator) and which is arranged parallel to the first assembly 22a, 24a but head-to-tail with respect thereto, is provided to enable the measurement of $n_3$, and possibly that of $n_4$: the data $n_3$ is supplied by the principal detector 23, the data $n_4$ being supplied by the second auxiliary detector 24b when it coccupies the position previously occupied by the source 22a at the instant of measuring of $n_1$. It has been demonstrated above that the use of $n_4$ is somewhat facultative, its only advantage being the replacement, in equation (1), of a unique data $\overline{n_1}$ by a mean value of $(n_1 + n_4)/2$.

Figure 8:
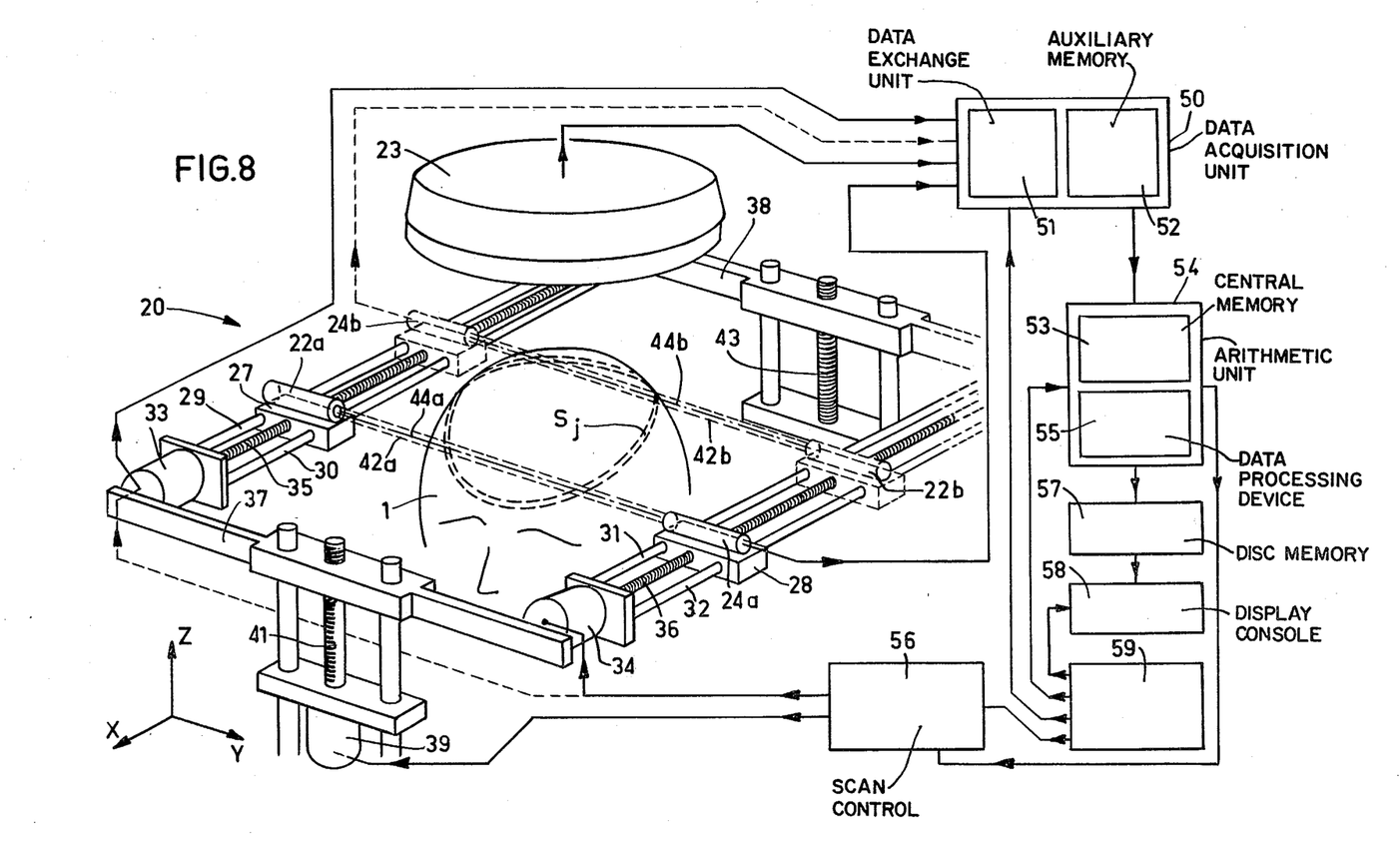
FIG. 8 is a detailed view of a first embodiment of the apparatus in accordance with the invention.

In FIG. 8, the source 22b and the auxiliary detector 24b are denoted by broken lines. Actually, instead of providing this second emission/detection assembly, use could be made of the same first assembly 22a, 24a for performing the measurements of $n_3$. In that case, after having performed a first scan of a slice, during which the data $n_1$ and $n_2$ are measured, the apparatus can be pivoted through 180° around the zone to be examined, so that the positions of the source 22a and the auxiliary detector 24a are permutated. In this new positon, a second scan of the same slice can be performed, again by means of the motors 33 and 34, thus enabling measurements of $n_3$ and, if desired, of $n_4$.

The measuring data $n_1$, $n_2$, $n_3$ and possibly of $n_4$, are acquired by a data acquisition unit 50; this unit comprises a data exchange unit 51 which serves to write in the auxiliary memory 52 the data $n_1$ (supplied by the auxiliary detector 24a), $n_2$ (supplied by the principal detector 23), $n_3$ (also supplied by the detector 23), $n_4$ (possibly supplied either by the auxiliary detector 24b, if present, or otherwise by the auxiliary detector 24a), a coordinate y (supplied by the principal detector 23), and a coordinate x (supplied by the position of the motors 33 and 34). These coordinates are defined in a reference pattern (OX, OY, OZ) of axes, extending perpendicularly two by two, which is shown at a bottom left of FIG. 8. The data $n_1$, $n_2$ etc. are written in the auxiliary memory 52 at a rate and as a measure of their acquisition during the irradiation of the slice examined, in this case the slice Sj.

When the acquisition of data for the slice Sj is terminated, these data are dispatched by the data acquisition unit 51 to the central memory 53 of an arithmetic unit 54 and are processed by a data processing device 55 in order to determine the electron density value in each of the volume elements Ei of the irradiated slice Sj. During this period, as soon as the transfer to the central memory 53 has been terminated, the arithmetic unit 54 instructs a scanning control unit 56 to proceed with the examination (and hence the irradiation) of the next slice $S_{j+1}$, controlled by the motors 39 and 40. The analysis of this slice $S_{j+1}$ and the introduction into the auxiliary memory 52 of the corresponding measuring data (x, y, $n_1$, $n_2$, $n_3$, and possibly $n_4$) are thus realized during the calculation of the density values concerning the slice Sj.

As has already been stated, this calculation utilizes previously calculated values, that is to say $T_{j-1}$ and $d_{i, j-1}$, which, therefore, have to be sustained in the central memory 53 until they have been used. After termination of the calculations concerning the slice Sj, the new values $T_j$ and $d_{i, j}$ have replaced in the central memory 53 the values $T_{j-1}$ and $d_{i, j-1}$ which were present therein (these new values will actually be used in all calculations concerning the slice $S_{j+1}$). During this period, the calculated electron density values $d_{i,j}$ are transferred on the one hand to the magnetic disc of a memory 57 and on the other hand to the image memory of a display console 58.

After acquisition of all results and calculation of all density values for the entire body to be examined, the storage of these values on a magnetic disc enables the user (generally, in medical applications a diagnostic) the possibility of instantly performing the transfer of density values of an arbitrary slice to the image memory of the display console 58 in order to permit a comparison of different slices of the zone examined.

Figure 9:
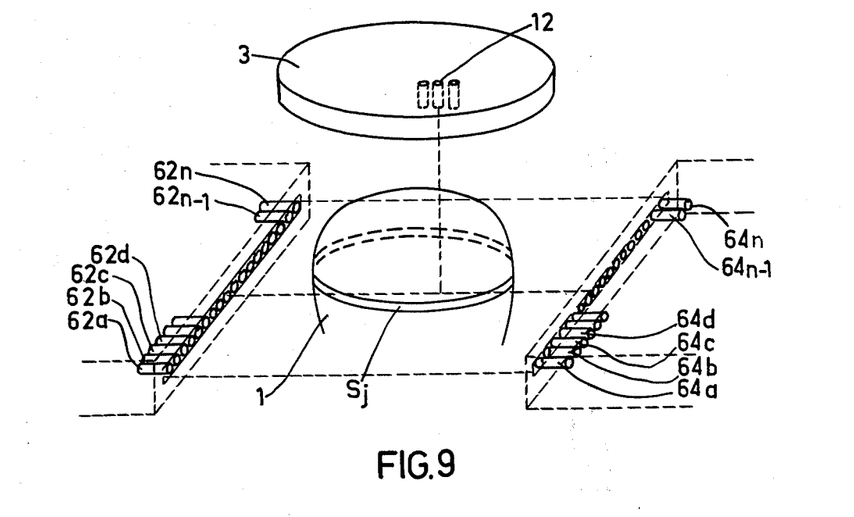
FIGS. 9 to 11 show three further embodiments of the apparatus in accordance with the invention.
Figure 10:
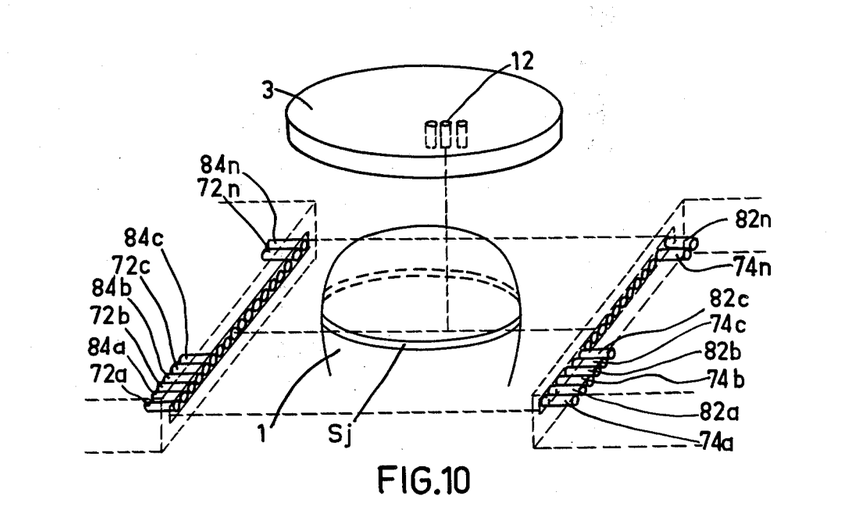

Three other embodiments of the apparatus in accordance with the invention can be elaborated and are described below with reference to the FIGS. 9 to 11.

The second embodiment proposed (FIG. 9) is analogous to that shown in the FIG. 8, with the following exception: instead of a single emission/detection assembly (22a, 24a), there are provided n juxtaposed identical assemblies (62a, 64a), (62b, 64b) ... (62i, 64i) ..., (62n, 64n) which on the one hand ensure the irradiation of each slice to be examined and which on the other hand provide measurement of the number $n_1$ of photons of each beam transmitted through the zone to be examined. This embodiment offers the advantage that the mechanical scanning device for the first direction is replaced by a stationary assembly of sources and auxiliary detectors which is associated with a commutation device for the sources 62a to 62n (a commutation device of this kind is known and is neither elaborated nor shown herein).

The third embodiment proposed (FIG. 10) differs from the embodiment shown in the FIGS. 8 and 9 only as follows: on the one hand there are provided n identical first emission/detection assemblies (72a, 74a) to (72n, 74n) which ensure irradiation of each slice to be examined during which the numbers $n_1$ and $n_2$ are measured, and on the other hand n second emission/detection assemblies (82a, 84a) to (82n, 84n), which are mutually identical and identical to the n first assemblies, but which are arranged head-to-tail with respect to these first arrangements, so that the beams emitted by the sources 72a to 72n and 82a to 82n overlap in a regularly alternating manner. These n second assemblies ensure irradiation of each slice to be examined, during which the numbers $n_3$ are measured and possibly also the numbers $n_4$. In this embodiment, the substantially increased complexity of the apparatus is advantageously compensated for by the elimination, during the execution of the examination process, of the source/detector permutation (which was necessary in order to perform the measurements of $n_3$ and $n_4$ after execution of the measurements of $n_1$ and $n_2$), and the quasi-elimination of the scanning in the first direction. This scan may in effect be replaced by a simple shifting, in the same direction, of the width of the beam emitted by the sources, which is realized either by shifting all emission/detection assemblies parallel to the plane of the slice examined or by displacement of the patient support and the principal detector by the same amount.

The shifting in the first scanning direction may even be completely omitted if the n first and the n second/emission detection assemblies (72a to n, 74a to n) and (82a to n, 84a to n) are no longer arranged in the plane of one and the same slice, but so that some assemblies irradiate one slice $S_{j-1}$ and the other assemblies the next slice $S_j$. In this case, the sources of one or the other of these two series of n assemblies may again be juxtaposed and the beams emitted thereby may be contiguous. However, this solution implies that the acquisition of data concerning a slice $S_j$ is not terminated until this slice has been successively irradiated by the n first emission/detection assemblies, followed by the n second assemblies; it also implies accurate asynchronization of the commutation device for the sources and the designation of memory locations corresponding to each volume element.

Figure 11:
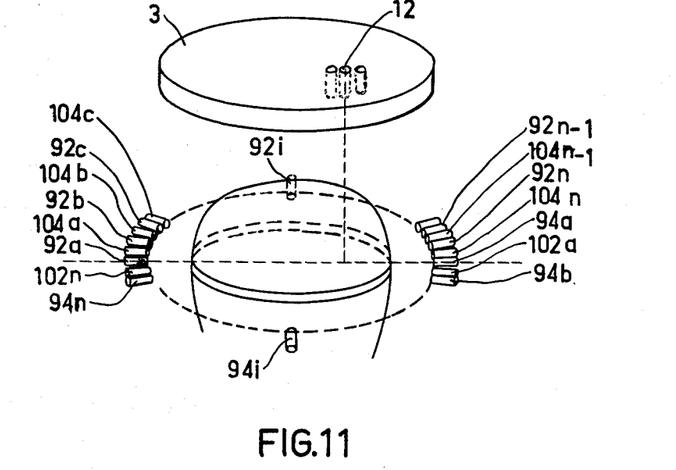

A fourth embodiment of the apparatus in accordance with the invention is proposed in FIG. 11. Its construction as well as its operation is analogous to that of the apparatus shown in FIG. 10, a difference consisting in that the n first and second emission/detection assemblies (92a to 92n, 94a to 94n) and (102a to 102n, 104a to 104n), respectively, are distributed around the zone 1 to be examined in a circular arrangement. Like in the third embodiment, this variant is characterized by the replacement, during the execution of the examination method, of the source/detector permutation by a simple rotating operation across the width of a beam. However, as before, this shifting may be eliminated if the n first assemblies are arranged so that they irradiate one slice $S_{j-1}$ while the n second assemblies are arranged to irradiate a slice $S_j$.

In the foregoing description it has been assumed that only the gamma ray source or sources and the principal detector are equipped with collimators. However, it is advantageous to provide a collimator also for each of the auxiliary detectors, because each of these auxiliary detectors is liable to receive not only the photons transmitted thereto by the corresponding, aligned source, but also those which arrive at the auxiliary detector, be it that they carry less energy, after having been subjected to several successive diffusions by the Compton effect inside the examined zone 1. This flux of diffused photons disturbs the measurements of $n_1$ and $n_4$. The presence of a collimator in front of each auxiliary detector substantially reduces the effect of these photons which have at least been diffused twice; actually, the auxiliary detector with which it is associated is thus rendered insensitive to any radiation which is not incident thereon according to a direction parallel to its longitudinal axis.

The presence of this collimator inter alia enables modification of the angle of aperture of the beam emitted by the source or sources by elimination or modification of the collimator of the latter; this modification, however, is envisaged only in a plane parallel to each slice, the aperture limit of this emitted beam in the direction perpendicular to the planes of the slices remaining indispensable for defining the thickness of these slices. This possibility of modification is useful notably in the case where the speed of examination is to be increased by the simultaneous irradiation of a larger surface of the zone to be examined and by activating several auxiliary detectors at the same time instead of one.

Photons which have been diffused several times also have a substantial effect on the measurements performed by the stationary principal detector 3. In order to reduce this effect, the detector 3 can be provided with an energy selection device. As the photons loose a fraction of their energy by each diffusion caused by the Compton effect which results in interactions between photons and electrons in the zone to be examined, the energy of the majority of the photons which have been diffused several times and which reach the detector 3 differs from that of the photons which have been diffused only once. By providing the gamme camera with an electronic circuit which serves as an energy window, an energy selection can be realized so that these photons which have been diffused several times are not taken into account during the measurements of the numbers $n_2$ and $n_3$.

The effect of photons which have been diffused a number of times on the measurements $n_2$ and $n_3$ can also be diminished by using a stationary principal detector in the form of a chamber with wires with electrodes extending in directions parallel to the axes OX and OY, respectively. The electrodes parallel to OY are in the blocked state, and an electric pulse is successively applied to each electrode thereof in order to achieve electrical unblocking of the corresponding zone of the detector which is situated exactly opposite the beam emitted by the source which is active at the relevant instant, that is to say situated in the plane defined by the beam and the detection axes of the principal detector which intercepts this beam. This zone in which the electrical unblocking of the principal detector is realized is displaced in synchronism with the scanning movement in the first scanning direction; therefore, only photons diffused several times but whose course is contained in this plane defined by the beam and the detection axes are detected. All other photons which have been diffused at least twice are no longer taken into account.

Figure 12:
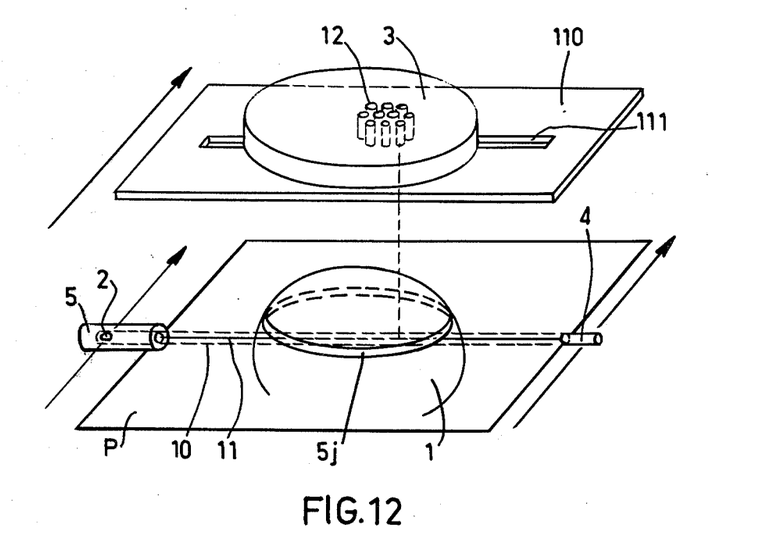
FIG. 12 shows an alternative embodiment of the principal radiation detector.

A substantially identical result is obtained when use is made of a principal detector without local blocking as described above, but equipped instead with a mechanical obturator such as the obturator 110 shown in the FIG. 12. An obturator of this kind, for example, made of lead or any other material having a high atomic number (tungsten, tantalum), comprises a rectilinear slit 111 and is displaced in front of the principal detector 3 in synchronism with the emission/detection assembly activated at the relevant instant. The obturator 110 absorbs all gamma rays which do not appear in front of the rectilinear slit 111.

It is to be noted that the present invention is not limited to the described and illustrated embodiments, on the basis of which other methods and other embodiments can be realized within the scope of the invention. Specifically, the cobalt 57 sources have been chosen for the apparatus because they are characterized by a strong flux of active photons per unit of volume and by the presence of a single emission peak at 122 KeV. This choice, however, is not limitative.

Moreover, the gamma camera chosen for the principal detector may notably be of the Anger type, which permits the use, if necessary, of the energy selection device with which this type of camera is equipped.

It is evident that also an image intensifier to be provided with on the one side an adequate collimator and on the other side with a television output system can be used as a principal detector. Upon using an image intensifier then the image pick-up tube of the TV system might be used as an integrator so that a slice can be completely scanned and then a second set of measuring data can be obtained by reading the charge stored on the sensitive target of the pick-up tube.

What is claimed is:
1. A method of tomographic examination for determining electron density by X-ray or gamma ray scanning of at least a part of a body to enable display of images of nominal slices, in which said part of the body is subdivided into volume elements defined by a nominal matrix in each slice, comprising the following steps:
   A. scanning a first slice in a first direction with a first collimated beam of penetrating radiation of known intensity which extends within the slice,
   detecting radiation within the beam which has passed through the slice to obtain a first set of measuring data $n_1$,
   simultaneously detecting Compton-scattered radiation which leaves the body in a direction perpendicular to the slice from each element in the slice, to obtain a second set of measuring data, $n_2$;
   B. scanning the first slice with a second substantially identical collimated beam of penetrating radiation in a direction which is opposite the first direction, detecting at least Compton-scattered radiation from each element in the slice which leaves the body in the direction perpendicular to the slice from each element in the slice, to obtain a third set of measuring data, $n_3$;
   C. storing the first, second and third sets of measuring data;
   D. calculating an electron density value in each element in the first slice on the basis of at least the first, second and third sets of measuring data;
   E. storing the electron density values in each element in the slice;
   F. scanning a further slice, adjacent to the slice most recently scanned, and detecting radiation per steps A and B to obtain at least further first, second and third sets of measuring data for the further slice;
   G. storing the further sets of measuring data;
   H. determining an electron density value in each element in the further slice on the basis of at least the further first, second and third sets of measuring data and the electron density values previously stored;
   I. storing the electron density values in each element in the further slice;
   J. repeating steps F, G, H, and I for a slice adjacent the slice most recently scanned until all slices within the part of the body to be examined have been scanned; and
   K. displaying the electron density values in elements of one or more of the slices.

2. The method as claimed in claim 1 further comprising the steps of detecting radiation within the beam which has passed through the slice during step B. and/or step F. to obtain a fourth set of measuring data, $n_4$, and combining the fourth set of measuring data with the corresponding first set of measuring data before determining the electron density values in the relevant slice.

3. The method of claim 2 wherein combining the first and fourth sets comprises averaging measuring data of the first and fourth sets for each beam path.

4. The method as claimed in claim 1 wherein the collimated beam of radiation is produced by at least one collimated source of penetrating radiation having a narrow spectrum and a given central frequency and contains a known number of photons having an energy which is sufficient to ensure that Compton diffusion is the predominant effect of interaction between those photons and electrons in the slice.

5. Tomography apparatus for determining electron density by X-ray or gamma ray scanning of at least a part of a body to enable display of images of nominal slices, in which said part of the body is subdivided into volume elements defined by a nominal matrix in each slice, comprising the following steps:
   A. scanning a first slice in a first direction with a first collimated beam of penetrating radiation of known intensity which extends within the slice,
   detecting radiation within the beam which has passed through the slice to obtain a first set of measuring data, $n_1$,
   simultaneously detecting Compton-scattered radiation emerging which leaves the body in a direction perpendicular to the slice from each element in the slice, to obtain a second set of measuring data, $n_2$;

B. scanning the first slice with a second substantially identical collimated beam of penetrating radiation in a direction opposite the first direction, detecting at least Compton-scattered radiation which leaves the body in the direction perpendicular to the slice from each element in the slice, to obtain a third set of measuring data, $n_3$;

C. storing the first, second and third sets of measuring data;

D. calculating an electron density value in each element in the first slice on the basis of at least the first, second and third sets of measuring data;

E. storing the electron density values in each element in the slice;

F. scanning a further slice, adjacent to the slice most recently scanned, and detecting radiation per steps A and B to obtain at least further first, second and third sets of measuring data for the further slice;

G. storing the further sets of measuring data;

H. determining an electron density value in each element in the further slice on the basis of at least the further first, second and third sets of measuring data and the electron density values previously stored;

which comprises:

collimated radiation source means for generating a beam of penetrating radiation in the first direction and for scanning a slice of the body with the beam which extends through the slice;

collimated principal radiation detector means for detecting radiation which emerges from the slice and leaves the body in a direction perpendicular to the first direction;

collimated auxiliary radiation detector means for detecting radiation leaving the slice within the beam;

a scanning control unit for controlling motion of the source means and the auxiliary detector means for scanning the slice;

a data acquisition unit for gathering at least the first, second and third measuring sets of data;

a memory for storing at least the first, second and third measuring sets of data;

a data processing device for determining electron density values in elements of the slice from at least the first, second and third measuring sets of data; and display means for displaying the electron density values determined by the data processing device.

6. Tomography apparatus as claimed in claim 5 wherein:

the principal radiation detector means are stationary and comprise a number of collimator openings which define a number of parallel detection axes and which have fixed elementary detection angles which cover the entire slice to be examined;

the radiation source and auxiliary detector means consist of an emission/detection assembly which is displaceable parallel to the first direction in a scanning direction perpendicular to the detection axes and which is further displaceable in a second direction which is substantially parallel to the detection axes.

7. Tomography apparatus as claimed in claim 5 wherein:

the principal radiation detector means are stationary and comprise a large number of collimator openings which correspond to a number of parallel detection axes and which have fixed elementary detection angles covering the entire slice to be examined; and the source and auxiliary radiation detector means comprise an emission/detection assembly which is rotatable around the slice to be examined in a first, circular scanning direction substantially perpendicular to the detection axes and is further displaceable in a second direction parallel to the detection axes.

8. Apparatus as claimed in claim 7 comprising a plurality of radiation sources and a like plurality of auxiliary radiation detectors each aligned with a corresponding one of the sources in order to constitute, in conjunction therewith, a array of emission/detection assemblies which are distributed in the first, circular scanning direction and further comprising means for sequentially commutating the operation of sources in the array.

9. Apparatus as claimed in any of claims 5 through 8 wherein the principal radiation detector means are a stationary gamma camera.

10. Apparatus as claimed in any of claims 5 through 8 further comprising an obturator having a rectilinear slit disposed between the principal detector means and the body, the slit being movable parallel to the scan slice.

11. Apparatus as claimed in any of claims 5 through 8 wherein each radiation source comprises cobalt 57.

* * * * *